United States Patent [19]

Wegrzyn

[11] Patent Number: 4,822,743
[45] Date of Patent: Apr. 18, 1989

[54] METHOD AND CLOTH FOR DETECTING LEAKS IN CLOSED BODIES

[75] Inventor: Jeffrey G. Wegrzyn, Alpharetta, Ga.

[73] Assignee: Lockheed Corporation, Calabasas, Calif.

[21] Appl. No.: 681,375

[22] Filed: Dec. 13, 1984

[51] Int. Cl.[4] .................... G01N 21/19; G01N 31/00
[52] U.S. Cl. ........................................ 436/3; 116/201; 116/206; 252/964; 422/56; 57; 436/163; 436/169
[58] Field of Search ................. 422/56, 57; 436/2, 3, 436/169, 163, 111; 116/201, 206; 252/964

[56] References Cited

U.S. PATENT DOCUMENTS

| 2,483,108 | 9/1949 | Silverman | 422/56 |
| 3,122,420 | 2/1964 | Rebar Jr. et al. | 422/56 |
| 3,146,070 | 8/1964 | Collins | 436/163 X |
| 3,238,020 | 3/1966 | Eiseman Jr. | 422/56 |
| 3,528,780 | 9/1970 | Radawski | 422/56 X |
| 3,544,484 | 12/1970 | Roth | 422/56 X |
| 3,580,704 | 5/1971 | Pickup et al. | 436/163 X |

FOREIGN PATENT DOCUMENTS 45-1875  1/1970  Japan .................................. 436/163

Primary Examiner—Barry S. Richman
Assistant Examiner—Jill Johnston
Attorney, Agent, or Firm—Robert P. Barton; Eric R. Katz; Stanley L. Tate

[57] ABSTRACT

A reusable indicating material for detecting leaks in sealed structures and other closed bodies comprises a fabric saturated with an indicator solution containing an acid-base indicator, a surfactant, a buffering system and a humectant. The indicator solution remains reactive when the fabric is dry to the touch and will indicate the presence of leaks in the structure being tested by changing color when a reactive gas escapes from the structure being tested. Upon removal from the tested structure the indicator material reverts to its original color and is available for subsequent tests.

10 Claims, No Drawings

METHOD AND CLOTH FOR DETECTING LEAKS IN CLOSED BODIES

TECHNICAL FIELD

This invention relates to an improved leak indicator and a method of using the same to detect fuel leaks in aircraft. More particularly, it relates to an improved leak indicator medium which is dry, can be reused and which does not stain painted surfaces being tested.

BACKGROUND ART

Leak detection is an essential aspect of the quality control in the construction of aircraft structures such as pressurized crew areas and fuel tanks. To check the integrity of such structures during and after construction a variety of methods are used for example, the structure is pressurized with air and a soap film is applied to the area being inspected and the formation of bubbles is visually noted. Another method involves pressurizing the structure being tested with ammonia gas and spraying the surface being tested with a viscous liquid which contains an acid-based indicator which will change color if a leak allows ammonia gas to escape. Still another method of testing for leaks involves pressurizing with a mass spectrometer. Leaks in fuel tanks may also be detected using thermographic techniques. Another method of detecting fuel leaks in both partially assembled or assembled aircraft involves applying an oil red O dyed talc to the surface being tested. The talc is applied by mixing it with 1,1,1 trichloroethane and spraying the mixture onto the surface being tested. The trichloroethane quickly evaporates leaving a pink powder on the test area. This method has been found to be an effective indicator of fuel tank leaks, however, the material used in the test procedure has several undesirable characteristics. The dye oil red O is a petroleum dye that is soluble in hydrocarbon solvents such as 1,1,1 trichloroethane and JP-5 jet fuel and this solubility causes some of the dye to migrate from the talc carrier into the surface of the paint used on the test area thereby staining it. Another undesirable characteristic is the similarity of the relation of the oil red O dye with water and its reaction to jet fuel. If either fuel or water contacts the oil red O impregnated talc the color of the talc changes from pink to red thus making the test meaningless if water is present as a mist, spray, or as falling rain. This characteristic of the dye decreases the usefulness of the test in the field.

U.S. Pat. No. 3,368,994 discloses a test indicating permanent finish or paint for use with missiles which detects leaks of mixed rocket fuel. The finish is specifically directed to detecting leaks which are mixtures of the amine fuel component and the red fuming nitric acid oxidizing component of rocket fuel. A fuel leak is indicated when the finish color changes color.

U.S. Pat. No. 3,287,156 discloses a leak indicating system which utilizes an undercoating and an overcoating both of which change color when exposed to leaking fuels and oxidizers. The undercoating generally comprises cellulose base laquers and solvent type resins with phenosofranine dispersed therein for the undercoating and phenolphthalein dispersed therein for the overcoating. Again, a coating color change indicates a leak.

U.S. Pat. No. 3,266,920 also discloses a leak indicating paint for liquid propellants of a base type and an oxidizer. More specifically, the indicator paint comprises a paint matrix and dispersed solids which include phenolphthalien and a coloring agent which is readily bleachable in the presence of the oxidizer component of rocket fuel.

U.S. Pat. No. 4,326,981 discloses a water base leak detecting solution consisting of a nonionic oxyalkylated aliphatic alcohol surfactant, a small amount of a dual visibility dye which will not migrate or penetrate into a painted aircraft surface and a non-parasitic agent. This solution is introduced into the fuel tanks and external surfaces are then viewed under suitable lighting conditions to locate leaks.

U.S. Pat. No. 4,361,035 discloses a "depuddling agent" which is introduced into a tank being tested with a U.S. Pat. No. 4,326,981 type tracer solution, to make residual tracer solution miscible with subsequently introduced oil or petroleum based fuel.

DISCLOSURE OF THE INVENTION

Accordingly, it is an object of the present invention to provide a low cost leak detection method which is applicable to any aircraft structure that does not require filling the structure being tested with fuel or oil.

Another object of the present invention is to provide a leak detection method which will not color or stain the surface being tested.

It is another object of the present invention to provide a dry indicator material capable of detecting leaks in aircraft structures without coloring or staining the surface being tested.

A further object of the present invention is to provide a reusable indicator material for detecting leaks in fuel containers, fuel tanks and pressurized areas of aircraft structure.

Still a further object of the present invention is to provide an indicator material which can be removed from a test surface without staining or otherwise damaging the test surface.

These and other objects, features and advantages of the present invention are accomplished by providing a material for and a method of detecting leaks in an aircraft structure, vessel, tank, container or other closed body which comprise a fabric impregnated with an indicator solution capable of detecting the presence of acid and basic materials in gaseous form even when the fabric is dry to the touch. The indicator is non-staining on painted surfaces and does not migrate into or penetrate painted surfaces containing a polyurethane or epoxy resin base or any other base material.

The new method of detecting leaks comprises the steps of providing a dry woven natural fiber cloth which has been impregnated with a solution containing an acid-base indicator, a surfactant, a buffering system and a humectant. The fabric is spread on the surface of a body or structure being tested which has been pressurized with a mixture of air and a gaseous composition which will react with the cloth borne solution to give a distinct change in the color of the cloth. The cloth is then observed for any color change because color change in the cloth resulting from a reaction between acid-base indicator is indicative of a leak either under or near the cloth. When the test is completed the cloth is removed from the surface being inspected and the reaction between the cloth borne solution and the gaseous test mixture is allowed to reverse itself thereby making the cloth ready for use in later tests.

The principal feature of the present invention is the provision of a dry indicator material and a method for using it to detect leaks in closed bodies such as aircraft structures, fuel tanks and the like without staining or otherwise damaging the painted surfaces of the test piece.

Another important feature of the present invention is the provision of an economical and reusable indicator material for use in locating leaks in closed bodies, such as aircraft structures, fuselages, fuel tanks and the like.

Yet another important feature of the present invention is the ease with which the indicator material can be used to inspect a test body for leaks.

Still another important feature of the present invention is elimination of messy cleanup procedures required to remove prior art indicators from surfaces being tested for leaks.

Another important feature of the present invention is the elimination of the necessity to fill fuel tanks with fuel or other liquid test solutions when testing them for leaks.

Another feature of the present invention is the elimination of the requirement to charge fuel tanks with depuddling agents after testing and prior to filling them with operational fuel loads.

One advantage of the present invention is that the present leak detection method complements other leak detection methods such as thermographic method which are used principally on unassembled sections and tanks.

Another advantage of the present leak detecting method is the non-staining nature of the indicator used reduces the cost of leak testing in that costly and time consuming cleanup after testing is eliminated.

Another advantage of the present invention is that the indicator material can be reused repeatably thereby substantially reducing the cost of leak testing aircraft structures and other closed bodies which are required to be free of leaks.

In accordance with the present invention the leak indicating material comprises a fabric impregnated with a solution containing an acid-base indicator, a surfactant, a buffering system, and a humectant with the balance being made up of water or other appropriate solvent. In some cases the solution will also include a thickener.

The present invention also comprises a method for detecting and locating leaks in aircraft structures and other closed bodies comprising the steps of providing a cloth woven from natural fiber material which is impregnated with a solution containing an acid-base indicator, a surfactant, a buffering system, and a humectant which is spread on the surface being inspected for leaks. The body being inspected is pressurized with a mixture of air and a gaseous composition which will react with the solution and cause the cloth to change color. When areas of local color change are observed their locations are observed and marked as the location of a leak.

In accordance with the present invention, any of the following surfactants may be used: alkylphenyl polyethylene glycol, which is sold by Rhom and Hass as Triton X-114; octylphenyl-polyethylene glycol ether as a 70 percent solution in water as sold by Rohm and Hass as Triton X-405; Surfynol TG-E which is a proprietary acetylenic diol blend sold by Air Products; (2,4,7,9-tetramethyl-5-deyn-4,7-diol) sold by Air Products as Surfynol 104; fluorosurfactants sold by DuPont as Zonyl FSN and Zonyl FSN-100; a potassium fluorinated alkyl carboxylate mixture sold by 3M as FC-128; a fluorinated alkyl quaternary ammonium iodide mixture sold by 3M as FC-134; and a fluorinated alkyl ester mixture sold by 3M as FC-430.

In accordance with the present invention humectants such as glycerine and poly(ethylene glycol) having an average molecular weight of about 3400 are used.

In accordance with the present invention the acid-base indicator is selected from a group consisting of phenol red, chlorophenol red, bromothymol blue, cresol purple, bromocresol purple, alizarin red S, and 2(2,4-dinitrophenylzao)-1-naphthol-3,6-disulfonic acid, disodium salt.

In accordance with the present invention a potassium hydrogen phthalate buffer system is used.

In accordance with the present invention an absorbent natural fiber cloth is saturated with the indicator solution and is allowed to air dry.

Ideally, the mixture of gases which will react with the solution and cause the cloth to change color is a mixture of ammonia gas and air which contains from about 1 percent ammonia to about 10 percent ammonia and from about 90 percent to about 99 percent air. Past results are obtained when the color change reaction will occur at at pH of from about 6 to about 9.

Also in accordance with the present invention the color change which the cloth undergoes is not permanent but is instead of a duration of from about 20 minutes to about 60 minutes after the cloth is removed from the presence of the reactive gas mixture.

These and other objects, features and advantages of the present invention will be more apparent from the following more detailed description of the preferred embodiments as hereinafter discussed and claimed.

BEST MODE FOR CARRYING OUT THE INVENTION

Generally, the invention includes a natural fiber cloth which is impregnated with an indicator solution and then allowed to dry so that when used the cloth is dry to the touch. The indicator solution consists of an acid-base indicator, a surfactant, a buffering system, a humectant, and a suitable solvent. While there are many acid-base indicators that can be used to detect the presence of aids and bases it has been found that the best results for applications such as detecting leaks in aircraft structures or fuel tanks are obtained when an indicator is used that changes to very contrasting colors such as from yellow to read. This is true because when the original color of the indicator is close to the color of the indicator after color change it is very difficult to see which makes it very difficult to discover such leaks. With this thought in mind phenol red has been determined to be the best indicator for use in sensitizing the cloth with the indicator solution. For example, when phenol red is used the cloth changes from yellow to red when an alkaline gas mixture such as ammonia and air is used to pressurize the structure being tested. It has also been found that acid base indicators which change color in the pH range 6 to 9 function well in the test environment.

The cloth which serves as the carrier of the indicator solution should be a woven variety freely permeable to gases, gaseous acids and gaseous bases, and preferably a cloth woven from a natural fiber because of the superior absorbency of natural fibers when compared to most synthetic fibers. Absorbency is a necessity because acid-base indicators require a liquid phase to react and change color thus making an ability to absorb and retain fluids essential if the indicator reaction is to occur on the cloth as is intended by the method of the present invention. In order to facilitate the uptake and retention of fluid by the cloth a humectant and a surfactant are included in the indicator solution. When an aqueous indicator solution is used a surfactant such as alkylphenylpolyethylenglycol (sold under the trade name of Triton GR-5 by Rhomand Hass) are used to lower the surface tension of the water thereby promoting the even distribution of the indicator solution throughout the cloth. It has also been found that a humectant such as glycerine must be present in sufficient quantity or the method will not function as intended. Without a minimum of about 3.0 to about 20.0 percent by weight humectant being present to bind the water in and around the cloth fibers and thereby provide the aqueous system necessary for the indication reaction to occur escaping alkaline gas mixture cannot be detected by the indicator impregnated cloth. In accordance with the present invention, preferably, the humectant concentration ranges from about 5 to about 15 percent by weight.

Good results have been obtained using an indicator solution having a formulation of from about 0.3 to about 2.0 weight percent Triton X-114, from about 2.0 to about 5.0 grams per liter potassium hydrogen phthalate, from about 0.05 to about 1.0 weight percent phenol red; 2.0 to about 20.0 weight percent glycerine and the balance consisting of either deionized or Type I reagent grade water. Poly(ethylene glycol) having an average molecular weight of 3400 may be used as a replacement from about 3.0 to about 5.0 percent of the glycerine, however, glycerine cannot be completely replaced and the polyethylene glycol can comprise no more than from about 3.0 to about 5.0 percent of the total indicator solution if best results are to be achieved.

It has been found that glycerine causes a brighter, more visible color and causes the cloth to retain its flexibility and prevents drying of the cloth. If the cloth drys out, its useful life is exhausted in that the indication reaction will no longer occur when the cloth is exposed to the reactive gas used to pressurize the sealed body being tested for leaks.

One example of a specific formulation tried is: 0.1 percent phenol red 0.05 Triton N-114, 5 grams per liter potassium hydrogen phlhalate buffer, 2.0 percent glycerine with the balance being made up of either deionized or Type I reagent grade water defined by ASTM standard D119. Tap water should be avoided when preparing the indicator solution because it tends to adversely affect the buffer system. A cloth saturated with this solution would have a shorter useful life than a cloth saturated with a solution in which the glycerine concentration is raised to about 10 percent.

When a cloth saturated with the indicator solution disclosed herein has been allowed to air dry it may than be either stored for later use or used to cover the critical areas of a sealed structure being inspected (joints and fasteners associated therewith) and observed for color changes caused by a reactive gas leak thereby bringing the indicator impregnated cloth into contact with the reactive gas. When all areas of color change have been observed and located the cloth can be removed from the body being tested and allowed to revert to its original color for subsequent reuse.

Obviously many modifications and variations of the present invention are possible in light of the above teachings. It is, therefore, to be understood that within the scope of the appended claims the invention may be practiced otherwise than as specifically described.

We claim:

1. A dry method of detecting leaks in aircraft structures and other closed bodies comprising the steps of:
    (a) providing a dry-to-the-touch woven, natural fiber cloth impregnated with a solution containing an acid-base indicator, a surfactant, a buffering system and humectant, said impregnated woven natural fiber cloth being freely permeable to both gaseous acids and gaseous bases and being sufficiently absorbent to be dry to the touch while retaining sufficient water in contact with reactive constituents of said solution to allow the acid-base indicator to react with a reactive gas escaping from a structure being tested;
    (b) spreading said cloth on the surface of an aircraft or other closed body which has been pressurized with a mixture of air and a gaseous composition which will react with said solution and cause a distinctive color change in the color of said cloth; and
    (c) observing said cloth for a color change indicative of said reaction so that the location of leaks in said structure or closed body become visible.

2. The method of claim 1 further including the steps of removing said cloth from said surface or closed body and allowing the reaction between said solution and said gaseous composition to reverse, so that said cloth reverts to its original color and is ready to be reused in subsequent tests.

3. The method of claim 1 wherein said providing of step (a) comprises impregnating said woven natural fiber cloth with said solution containing said acid-base indicator, said surfactant, said buffering system,, said humectant with the balance being made up of deionized water.

4. The method of claim 3 wherein said acid base indicator is selected from the group consisting of phenol red, chlorophenol red, bromothymol blue, cresol purple, bromocresol purple, alizarin reds and 2 (2,4-dinitrophenyl-azo)-1-naphthal-3-6 disulfonic acid, disodium salt.

5. The method of claim 3 wherein said buffering system is potassium hydrogen phthalate.

6. The method of claim 3 wherein said humectant is glycerin.

7. The method of claim 3 wherein said humectant is a mixture of glycerin and poly (ethylene glycol) wherein said poly (ethylene glycol) has an average molecular weight of about 3400 and comprises no more than from about 3.0 to about 5.0 percent of the total indicator solution.

8. The method of claim 3 wherein said solution consists of from about 0.05 weight percent to about 1.0 weight percent phenol red, and from about 2 to about 5 grams per liter potassium hydrogen phthalate and from about 0.3 weight to about 2.0 weight percent surfactant and about 2.0 weight percent humectant with the balance being made up of deionized or Type I reagent grade water.

9. The method of claim 3 wherein the humectant concentration is from about 5 to about 15 percent by weight.

10. The method of claim 3 wherein said surfactant is selected from a group consisting of: alkylphenyl polyethylene glycols; octyl phenyl—polyethylene glycol ethers; acetylenic diols; 2,4,7,9-tetramethyl-5-deyn-4,7-diol; potassium fluorinated alkyl carboxylates; fluorinated alkyl quaternary ammonium iodides; and fluorinated alkyl esters.

* * * * *